United States Patent
Funk et al.

(10) Patent No.: US 6,297,335 B1
(45) Date of Patent: Oct. 2, 2001

(54) CROSSLINKED, HYDROPHILIC, HIGHLY SWELLABLE HYDROGELS, PRODUCTION THEREOF AND USE THEREOF

(75) Inventors: Rüdiger Funk, Niedernhausen; Norbert Herfert, Altenstadt; Mariola Wanior, Erlensee, all of (DE); Patricia D. Brown, Portsmouth, VA (US); Fritz Engelhardt; Guy T. Woodrum, both of Chesapeake, VA (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/245,298

(22) Filed: Feb. 5, 1999

(51) Int. Cl.$^7$ ..................... C08F 222/02; C08F 222/38; C08F 220/04; C08F 220/06
(52) U.S. Cl. ..................... 526/317.1; 526/278; 526/287; 526/240; 526/303.1; 526/318.2; 526/320
(58) Field of Search ................. 526/317.1, 320, 526/303.1, 240, 278, 287, 318.2

(56) References Cited

U.S. PATENT DOCUMENTS

| | | | | |
|---|---|---|---|---|
| 5,115,011 | * | 5/1992 | Harada | 524/419 |
| 5,185,413 | * | 2/1993 | Yoshinaga | 526/233 |
| 5,886,678 | * | 2/1999 | Kajikawa | 528/487 |
| 6,107,358 | * | 8/2000 | Harada | 521/133 |
| 6,110,992 | * | 8/2000 | Wada | 523/200 |

* cited by examiner

*Primary Examiner*—Fred Zitomer
(74) *Attorney, Agent, or Firm*—Oblon, Spivak, McClelland, Maier & Neustadt, P.C.

(57) ABSTRACT

The hydrogels are based on polymerized monomers or on graft polymers and each have a Pressure Absorbency Index <100 and a vertical absorption of not less than 12 g/g under a pressure of 1922.8 Pa. They are produced by free-radically polymerizing hydrophilic monomers which contain acid groups, or their alkali metal or ammonium salts, with (a) a copolymerization crosslinker which contains at least two ethylenically unsaturated double bonds in the molecule, and (b) a reactive crosslinker A which contains an ethylenically unsaturated double bond and at least one functional group capable of forming covalent bonds with the acid groups of the hydrophilic polymers, a reactive crosslinker B which contains at least two functional groups capable of forming covalent bonds with the acid groups of the hydrophilic polymers, and/or with ions of polyvalent metals optionally in the presence of at least one grafting base to form a crosslinked, hydrophilic base polymer, comminuting said base polymer and postcrosslinking the surface of the particles of said base polymer, and are useful as absorbents for water and aqueous fluids.

14 Claims, No Drawings

CROSSLINKED, HYDROPHILIC, HIGHLY SWELLABLE HYDROGELS, PRODUCTION THEREOF AND USE THEREOF

SPECIFICATION

The present invention relates to crosslinked, hydrophilic, highly swellable hydrogels having a Pressure Absorbency Index <100 and a vertical Absorption of not less than 12 g/g under a pressure of 1922.8 Pa, a process for production thereof and use thereof.

Hydrophilic hydrogels obtainable by polymerization of unsaturated acids, for example acrylic acid or methacrylic acid or acrylamidopropanesulfonic acid, in the presence of small amounts of polyolefinically unsaturated compounds are already known as superabsorbent polymers. They are described for example in U.S. Pat. Nos. 4,057,521, 4,062,817, 4,525,527, 4,286,082, 4,340,706 and 4,295,987.

Also known are hydrophilic hydrogels obtainable by graft copolymerization of olefinically unsaturated acids on different matrices, for example polysaccharides, polyalkylene oxides and derivatives thereof; cf. for example U.S. Pat. Nos. 5,011,892, 4,076,663 and 4,931,497.

The hydrogels mentioned have high absorption capacity for water and aqueous solutions and are therefore the preferred superabsorbent polymers for use as absorbents in hygiene articles.

The increasing tendency to make hygiene articles such as baby and adult incontinence diapers ever smaller and thinner while preserving the same total absorption capacity is contingent on the ability to reduce the proportion of bulky wood pulp fluff and to raise the proportion of highly swellable hydrogel. As a consequence, the superabsorbent polymers have to perform additional functions with regard to liquid acquisition, transportation and distribution which were previously performed by the wood pulp fluff in order that any leakage of the hygiene article due to the phenomenon known as gel blocking may be prevented.

U.S. Pat. No. 5,147,343 discloses absorbent compositions comprising a porous fiber matrix and an amount of superabsorbent polymer dispersed in the pores of the fiber matrix. The superabsorbent polymer can absorb at least 27 ml of a 0.9% strength by weight sodium chloride solution under a restraining pressure of 21,000 dyn/cm$^2$. The amount of superabsorbent polymer in the absorbent composition is preferably 10–60% by weight.

U.S. Pat. No. 5,149,335 describes absorbent structures comprising 60–100% by weight of superabsorbent polymer. The superabsorbent polymer is characterized by a Free-Swell Rate of less than 60 s and a 5-minute AUL (absorption under load) value of at least 15 g/gs EP-A-0 532 002 discloses absorbent compositions comprising a porous fiber matrix and at least 30% by weight of superabsorbent polymer, the superabsorbent polymer having a Deformation Under Load-of 0.60 mm or less and a Wicking Index of 10 cm or more.

EP-A-0 615 736 relates to absorbent compositions comprising 30–100% by weight of superabsorbent polymer having a Pressure Absorbency Index of at least 100 and an extractables content (16 h extraction in 0.9% strength by weight aqueous sodium chloride solution) of less than 13% by weight.

EP-A-0 761 191 describes absorbent compositions comprising a fiber matrix and at least 30% by weight of superabsorbent polymer having a Wicking Parameter of 700 or more.

U.S. Pat. No. 5,562,646 discloses an absorbent composition comprising at least one region having a superabsorbent polymer in a concentration of 60–100% by weight, the superabsorbent polymer having a porosity of at least 0.15 and a Performance Under Pressure value of at least 23 g/g under a confining pressure of 0.7 psi (4826.5 Pa).

U.S. Pat. Nos. 5,599,335 and 5,669,894 describe absorbent compositions comprising at least one region having a superabsorbent polymer in a concentration of 60–100% by weight, the superabsorbent polymer having a Saline Flow conductivity value of at least $30 \times 10^{-7}$ cm$^3$sec/g and a Performance Under Pressure value of at least 23 g/g under a confining pressure of 0.7 psi.

Although the use of prior art superabsorbent polymers has improved the quality of highly hydrogel-loaded hygiene articles compared with the use of minimally crosslinked, non-surface-postcrosslinked superabsorbent polymer products of the 1st generation, prior art superabsorbent polymers in these hygiene articles all exhibit disadvantages with regard to liquid acquisition, transportation and distribution, so that there are limits to increasing the proportion of highly swellable hydrogel in the diaper due to the attendant loss of quality.

It is an object of the present invention to provide a highly swellable hydrogel which does not have the above-described disadvantages and which exhibits excellent acquisition and retaining characteristics for body fluids even when used in diaper constructions having a very high proportion of superabsorbent polymer.

We have found that this object is achieved by a crosslinked, hydrophilic, highly swellable hydrogel based on polymerized monomers or based on graft polymers, characterized by a Pressure Absorbency Index <100 and a vertical Absorption of not less than 12 g/g under a pressure of 1922.8 Pa. Particular preference is here given to hydrogels having a Performance under Pressure value of less than 23 g/g under a confining pressure of 0.7 psi (4826.5 Pa), and/or an Absorbency Under Load (AUL) value of less than 27 g/g under a confining pressure of 21,000 dyn/cM$^2$ (2100 Pa). The extremely high crosslinking of the hydrogels is obtained using a process for producing the crosslinked, hydrophilic, highly swellable hydrogels, which comprises free-radically polymerizing hydrophilic monomers which contain acid groups, or their alkali metal or ammonium salts, with (a) a copolymerization crosslinker which contains at least two ethylenically unsaturated double bonds in the molecule, and (b) a reactive crosslinker A which contains an ethylenically unsaturated double bond and at least one functional group capable of forming covalent bonds with the acid groups of the hydrophilic polymers, a reactive crosslinker B which contains at least two functional groups capable of forming covalent bonds with the acid groups of the hydrophilic polymers, and/or with ions of polyvalent metals optionally in the presence of at least one grafting base to form a crosslinked, hydrophilic base polymer, comminuting said base polymer and postcrosslinking the surface of the particles of said base polymer. A surface postcrosslinking of the base polymers initially obtained increases the crosslinking density of the surface even further.

In what follows, the highly crosslinked, hydrophilic, highly swellable hydrogels of the present invention and the process for their production will be more particularly described.

Hydrophilic monomers useful for producing the water-swellable hydrophilic polymers of the present invention include for example polymerization-capable acids, such as acrylic acid, methacrylic acid, vinylsulfonic acid, vinylphosphonic acid, styrenesulfonic acid, maleic acid including its anhydride, fumaric acid, itaconic acid, 2-acrylamido-2-methylpropanesulfonic acid, 2-acrylamido-2-methylpropanephosphonic acid and also their amides, hydroxyalkyl esters and amino group- or ammonium group-containing esters and amides. Also, water-soluble N-vinylamides or else diallyldimethylammonium chloride.

Preferred hydrophilic monomers are compounds of the general formula (I)

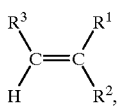
(I)

where $R^1$ is hydrogen, methyl or ethyl, $R^2$ is a —$COOR^4$ group, a sulfonyl group, a phosphonyl group, a phosphonyl group esterified with ($C_1$–$C_4$) alkanol or a group of the formula

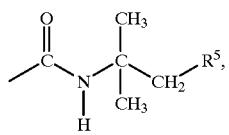
(II)

$R^3$ is hydrogen, methyl, ethyl or carboxyl, $R^4$ is hydrogen, an alkali metal ion or an ammonium ion, and R5 is sulfonyl, phosphonyl or carboxyl.

Examples of ($C_1$–$C_4$) alkanols are methanol, ethanol, n-propanol, isopropanol and n-butanol.

Particularly preferred hydrophilic monomers are acrylic acid and methacrylic acid.

Suitable grafting bases may be of natural or synthetic origin. Examples are starch, cellulose and cellulose derivatives, and also other polysaccharides and oligosaccharides, polyvinyl alcohol, polyalkylene oxides, especially polyethylene oxides and polypropylene oxides or block copolymers of ethylene oxide and propylene oxide, and also hydrophilic polyesters. Suitable polyalkylene oxides have for example the formula

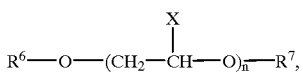
(III)

where $R^6$ and $R^7$ are independently hydrogen, alkyl, alkenyl or aryl,

X is hydrogen or methyl, and n is an integer from 1 to 10,000, $R^6$ and $R^7$ are each preferably hydrogen, $C_1$–$C_4$-alkyl, $C_2$–$C_6$-alkenyl or phenyl.

The amount of at least one grafting base used per 100 parts by weight of the monomers used in the polymerization is for example within the range from 0 to 30, preferably from 0 to 10, parts by weight.

The highly swellable hydrogels of the present invention are produced by the conjoint use of copolymerization and reactive crosslinkers and/or ions of polyvalent metals.

copolymerization crosslinkers are compounds having at least two double bonds in the molecule, which are copolymerizable with the hydrophilic monomers suitable for producing the water-swellable hydrophilic polymers of the present invention. Suitable copolymerization crosslinkers are especially methylene-bisacrylamide and methylenebismethacrylamide, esters of unsaturated mono- or polycarboxylic acids of polyols, such as diacrylate or triacrylates, e.g., butanediol diacrylate, butanediol dimethacrylate, ethylene glycol diacrylate, ethylene glycol dimethacrylate and also trimethylolpropane triacrylate, allyl compounds such as allyl (meth)acrylate, triallyl cyanurate, diallyl maleate, polyallyl esters, tetraallyloxyethane, triallylamine, tetraallylethylenediamine, pentaerythritol triallyl ether or allyl esters of phosphoric acid and also vinyl compounds such as vinyl acrylate, divinyl adipate, divinylbenzene and vinylphosphonic acid derivatives as described for example in EP-A 343 427. Preference is given to the use of allyl and (meth)acrylate crosslinkers. These crosslinkers are used in the polymerization for example in amounts from 0.1 to 5.0%, preferably from 0.5 to 3.0%, by weight, based on the hydrophilic monomers.

Reactive crosslinkers a are compounds which contain at least two functional groups capable of reacting with the functional groups of the copolymerized hydrophilic monomers, for example the carboxyl groups of acrylic acid, to form ionic and/or covalent bonds. Examples of such compounds are polyhydric alcohols, polyacid amines, polyamidoamines and their reaction products with epichlorohydrin, di- and polyepoxides, bis- and polyaziridines, bis- and polyoxazolines, di- and polyisocyanates, ethylene carbonate, propylene carbonate, 2-oxazolidone and its derivatives, polyethyleneimines, poly(diallyldimethylammonium chloride), polyvinylamines, and also all salts of polyvalent metal ions. Preference is given to the use of polyamidoamines and their reaction products with epichlorohydrin or with bischlorohydrin ethers of polyethylene glycols, polypropylene glycols or block copolymers of ethylene oxide and propylene oxide each having molar masses of up to 6000 and also of aluminum salts such as, for example, sodium aluminate. The reactive crosslinkers B are used in the polymerization for example in amounts from 0.05 to 7.5% by weight, based on the hydrophilic monomers, or after the polymerization and a comminuting of the resulting hydrophilic gels in amounts of for example from 0.02 to 3.0%, preferably from 0.04 to 2.0%, by weight, based on the polymers.

It is further possible to use compounds having both the character of a copolymerization crosslinker and the character of a reactive crosslinker. These compounds are hereinafter called reactive crosslinkers A. These compounds have at least one double bond in the molecule capable of entering a copolymerization with the hydrophilic monomers suitable for producing the water-swellable hydrophilic polymers of the present invention and at least one functional group capable of reacting with the functional groups of the hydrophilic monomers suitable for producing the water-swellable hydrophilic polymers of the present invention, for example the carboxyl groups of acrylic acid, to form ionic and/or covalent bonds. Examples of such compounds are glycidyl methacrylate and 2-hydroxyethyl (meth)acrylate. This group of crosslinkers is used in the production of the polymers.

Based on the hydrophilic monomers used in the polymerization, for example, from 0.1 to 5.0% by weight is used of crosslinkers A which contain a double bond and at least one functional group capable of forming a covalent bond with the acid groups of the hydrophilic polymers.

A preferred embodiment of the inventive process for producing the crosslinked, hydrophilic, highly swellable hydrogels comprises free-radically polymerizing hydrophilic monomers which contain acid groups, or their alkali metal or ammonium salts, with (a) a copolymerization crosslinker which contains at least two ethylenically unsaturated double bonds in the molecule, and optionally (b) a reactive crosslinker A which contains an ethylenically unsaturated double bond and at least one functional group capable of forming covalent bonds with the acid groups of the hydrophilic polymers, optionally in the presence of a grafting base to form a crosslinked, hydrophilic base polymer, comminuting said base polymer, during said comminuting or thereafter mixing it with a reactive crosslinker B and/or with ions of polyvalent metals and postcrosslinking the surface of the particles of said base polymer. Sodium aluminate is advantageously used for postcrosslinking the surface of the particles of the base polymer.

To initiate the polymerization it is possible to use high energy electromagnetic radiation or the customary chemical polymerization initiators, for example organic peroxides, such as benzoyl peroxide, tert-butyl hydroperoxide, methyl ethyl ketone peroxide, cumene hydroperoxide, azo compounds such as azobisisobutyronitrile and also inorganic peroxo compounds such as ammonium persulfate, potassium persulfate or hydrogen peroxide, optionally in combination with reducing agents such as sodium bisulfite, and iron(II) sulfate or redox systems in which the reducing component is an aliphatic or aromatic sulfinic acid, such as benzenesulfinic acid or toluenesulfinic acid or derivatives of this acid, for example adducts of sulfinic acid, aldehydes and amino compounds.

Preference is given to a polymerization in aqueous solution by the gel polymerization process and by utilizing the Trommsdorff-Norrish effect, cf. Makromol. Chem. 1, 169 (1947). The polymerization may be carried out both batchwise and continuously.

While the addition of the copolymerization crosslinkers and of crosslinkers A which contain a double bond and at least one reactive group must always take place to the monomer solution prior to initiation or during the polymerization, the reactive crosslinkers B and the ions of polyvalent metals may be added either to the monomer solution or after the polymerization is complete. In the latter case, the gel is advantageously first comminuted in suitable apparatus and then for example reacted with the reactive crosslinkers B and/or ions of polyvalent metals in a kneader or mincer. The copolymerization crosslinkers used are preferably compounds having at least two allyl, methacrylate and/or acrylate groups. Preferred reactive crosslinkers B are for example polyamidoamines and their reaction products with epichlorohydrin or bischlorohydrin ethers of alkylene glycols or polyalkylene glycols. Also of interest is the use of sodium aluminate as crosslinker component (b). In a preferred process variant, the copolymerization of the hydrophilic monomers which contain acid groups is carried out in the presence of (a) allyl methacrylate, tetraallyloxyethane, methylenebisacryl-amide, pentaerythritol triallyl ether or mixtures thereof, and (b) hydroxyethyl acrylate, hydroxyethyl methacrylate, hydroxypropyl acrylate, hydroxypropyl methacrylate, hydroxybutyl acrylates or mixtures thereof as crosslinker.

The hydrogel particles are dried by processes which are known to the person skilled in the art, for example by the rotating drum process with the aid of drum dryers or by the conveyor belt process whereby foraminous trays of a circular conveyor are loaded in a tunnel with material to be dried and the material to be dried is dried during conveyance by hot air being blown through the tray holes.

The particle size distribution of the dried and optionally precomminuted hydrogel is set by grinding, the particle size of the hydrogel particles generally being within the range from 50 to 2000 $\mu$m, preferably within the range from 100 to 1000 $\mu$m.

To produce the highly crosslinked, hydrophilic, highly swellable hydrogels of the present invention, the crosslinked base polymer hydrogel initially obtained is subjected to a subsequent surface postcrosslinking. To this end, compounds capable of reacting with the functional groups of the hydrogel in a crosslinking reaction (reactive crosslinkers B and ions of polyvalent metals) are applied to the surface of the hydrogel particles, preferably in the form of an aqueous solution. Suitable postcrosslinking agents were mentioned above in connection with the reactive crosslinkers. They are for example di- or polyglycidyl compounds such as phosphonic acid diglycidyl ether or ethylene glycol diglycidyl ether, alkoxysilyl compounds, polyaziridines, polyamines or polyamidoarines and also their reaction products with epichlorohydrin, polyols such as ethylene glycol, 1,2-propanediol, 1,4-butanediol, glycerol, di- and polyglycerol, pentaerythritol,sorbitol, the ethoxylates of these polyols and their esters with carboxylic acids or carbonic acid such as ethylene carbonate or propylene carbonate, oxazolidone and its derivatives, bisoxazoline, polyoxazolines, di- and polyisocyanates. If necessary, acidic catalysts such as, for example, p-toluenesulfonic acid, phosphoric acid, boric acid or ammonium dihydrogenphosphate can be added. For the postcrosslinking, for example, from 0.001 to 5.0%, preferably from 0.01 to 1.0%, by weight of at least one of the postcrosslinking agents mentioned are used per 100 parts by weight of base polymer hydrogel. Preferred crosslinking agents are diglycidyl ethers, reaction products of polyamidoamines with epichlorohydrin, bischlorohydrin ethers of alkylene glycols or polyalkylene glycols, polyethyleneimines, polymers containing vinylamine units or a mixture thereof.

Suitable mixing apparatus for spraying the crosslinker solution onto the hydrogel particles includes for example Patterson-Kelly mixers, DRAIS turbulence mixers, Lddige mixers, screw mixers, plate mixers, fluidized bed mixers, Schugi-Mix. The spraying on of the crosslinker solution may be followed by a temperature treatment step, preferably in a downstream dryer, at a temperature within the range from 80 to 230° C., preferably 80–190° C., particularly preferably within the range from 100 to 160° C., for a period of from 5 minutes to 6 hours, preferably from 10 minutes to 2 hours, particularly preferably from 10 minutes to 1 hour, in which case not only cracking products but also solvent residues may be removed.

In a particular embodiment of the invention, the hydrophilicity of the hydrogel particle surface is additionally modified by formation of metal complexes. The metal complexes are formed on the outer shell of the hydrogel particles by spraying on solutions of divalent or higher metal salts whose metal cations are capable of reacting with the functional groups of the hydrogel to form complexes. Examples of divalent or higher metal cations are $Mg^{2+}$, $Ca^{2+}$, $Al^{3+}$, $Sc^{3+}$, $Ti^{4+}$, $Mn^{2+}$, $Fe^{2+/3+}$, $Co^{2+}$, $Ni^{2+}$, $Cu^{+/2+}$, $Zn^{2+}$, $Y^{3+}$, $Zr^{4+}$, $Ag^+$, $La^{3+}$, $Ce^{4+}$, $Hf^{4+}$, and $Au^{+/3+}$, preferred metal cations are $Mg^{2+}$, $ca^{2+}$, $Al^{3+}$, $Ti^{4+}$, $Zr^{4+}$ and $La^{3+}$, and particularly preferred metal cations are $Al^{3+}$, $Ti^{4+}$ and $Zr^{4+}$. The metal cations may be used both alone and mixed with each or one another. Of the metal cations mentioned, any metal salt is suitable which possesses sufficient solubility in the solvent to be used. Particularly suitable metal salts have weakly complex anions such as for example chloride, nitrate and sulfate. Suitable solvents for the metal salts include water, alcohols, dimethylformaride, dimethyl sulfoxide and also mixtures thereof. Particular preference is given to water and water/alcohol mixtures such as, for example, water/methanol or water/1,2-propanediol.

The spraying of the metal salt solution onto the hydrogel particles may take place both before and after the surface postcrosslinking of the hydrogel particles. In a particularly preferred process, the spraying on of the metal salt solution takes place in the same step as the spraying on of the crosslinker solution, the two solutions being sprayed on separately in succession or simultaneously via two nozzles, or crosslinker and metal salt solution may be sprayed on via a single nozzle.

Optionally, the hydrogel particles may be further modified by admixture of finely divided inorganic solids, for example silica, aluminum oxide, titanium dioxide and iron(II) oxide to further augment the effects of the surface aftertreatment. Particular preference is given to the admixture of hydrophilic silica or of aluminum oxide having an average primary particle size of from 4 to 50 nm and a specific surface area of 50–450 $m^2/g$. The admixture of finely divided inorganic solids preferably takes place after the surface modification through crosslinking/complexing, but may also be carried out before or during these surface modifications The crosslinking density of the hydrogels can be determined by measuring the absorption capacity with and without restraining pressure. A particularly suitable method for this purpose is the Pressure Absorbency Index, which is described in EP 0 615 736 and which represents the sum of the values for the absorption under 4 different loads, namely AUL 0.01 psi (69 Pa), AUL 0.29 psi (1999.5 Pa), AUL 0.57 psi (3930 Pa) and AUL 0.90 psi (6205.3 Pa). Further methods for measuring the absorption capacity are the Performance Under Pressure (PUP) value, which is measured under a restraining pressure of 0.7 psi (4826.5 Pa) as described in U.S. Pat. No. 5,562,646, and the Absorbency Under Load (AUL) which is measured under a restraining pressure of 21,000 $dyn/cm^2$ (2100 Pa) as described in U.S. Pat. No. 5,147,343.

Fluid transportation and distribution in a swollen hydrogel layer can be characterized by measuring the Vertical Absorption under pressure and also by measuring the Acquisition Time/Rewet under pressure. These test methods are described hereinbelow.

The hydrogels of the present invention possess extremely high crosslinking. The hydrogel has a Pressure Absorbency Index <100 and also a Vertical Absorption under pressure of not less than 12 g/g. Particular preference is given to such hydrogels which additionally possess a Performance Under Pressure value of less than 23 g/g under a confining pressure of 0.7 psi (4826.5 Pa) and/or an Absorbency under Load (AUL) value of less than 27 gg under a confining pressure of 21,000 $dyn/cm^2$ (2100 Pa).

The hydrogels of the present invention are notable for excellent properties with regard to liquid acquisition, transportation and distribution and are therefore particularly useful as absorbents for water and aqueous fluids, especially body fluids, for example urine or blood, for example in hygiene articles such as for example baby and adult diapers, sanitary napkins, tampons and the like. However, they can also be used as soil improvers in agriculture and horticulture, as moisture binders in cable sheathing and also for thickening aqueous wastes.

Description of Test Methods vertical Absorption Under Pressure

The test apparatus required for measuring the vertical absorption under pressure consists of measuring cells and a liquid container. The measuring cells represent a cylindrical Plexiglass tube 2.6 cm in internal diameter and 15 cm in length. The upper end of the tube is open, the lower end possesses a 36 µm sieve bottom. At a height of 3 cm (from the lower end of the tube) the tube possesses a supporting ring. The liquid container is a Plexiglass box 30.0 cm in length, 20.5 cm in width and 3.8 cm in height. A 2 cm high overflow wall is fitted at a distance of 1.5 cm from one transverse side. On the side opposite is a connection to the liquid container, so that a constant level of liquid is ensured. The Plexiglass box has a removable lid which is provided with 6 circularly round holes each 3.2 cm in diameter. To perform the measurement, 2 g of hydrogel are weighed into a measuring cell, and the hydrogel particles are uniformly distributed over the sieve bottom. The hydrogel particles are then covered with a close clearance Plexiglass disk and a close clearance Plexiglass cylinder with metal rod is introduced, the total weight of the Plexiglass disk and of the cylinder with rod being 100 g, so that the hydrogel particles are under a pressure of 19.6 $g/cm^2$. The liquid container is filled with 0.9% strength by weight sodium chloride solution. The measuring cell is then introduced through a hole in the lid and dipped into the liquid (to depth of 12 cm) the measuring cell being held by the supporting ring. At any one time, up to 6 measuring cells can be measured. The measuring cells are left in the liquid container for 60 minutes, during which the hydrogel particles swell and increase in weight by absorbing liquid against the force of gravity. Owing to the very high surface coverage due to the hydrogel particles, very good conveyance of liquid is required to achieve a high swell level. After 60 minutes, the measuring cell is removed from the liquid container and the absorbed amount of liquid is determined by weighing. The vertical absorption under pressure is obtained by dividing the amount of liquid absorbed by the original weight of hydrogel.

Acquisition Time/Rewet Under Pressure

The test is carried out using laboratory pads. So produce these laboratory pads, 11.2 g of cellulose fluff and 23.7 g of hydrogel are homogeneously fluidized in an air box and by application of a slight vacuum laid down on a mold 12 by 26 cm in size. This composition is then wrapped in tissue paper and compressed for 2 times 15 seconds under a pressure of 200 bar. A laboratory pad produced in this way is attached to a horizontal surface. The center of the pad is determined and marked. Synthetic urine solution is applied through a plate of plastic having a ring in the middle (internal diameter of ring: 6.0 cm, height: 4.0 cm). The plate is loaded with additional weights so that the total load on the pad is 13.6 $g/cm^2$. The plate of plastic is placed on the pad in such a way that the center of the pad is also the center of the application ring. 80 ml of synthetic urine solution are applied 3 times.

The synthetic urine solution is prepared by dissolving 1.26 g of magnesium sulfate heptahydrate, 3.75 g of potassium chloride, 6.33 g of sodium chloride, 15.00 g of urea, 2.50 g of potassium dihydrogenphosphate and 1.22 g of sodium hydrogenphosphate dihydrate in 1 kg of demineralized water. The synthetic urine solution is measured out in a measuring cylinder and applied in one shot to the pad through the ring in the plate. At the same time, the time is measured until the solution has completelypenetrated into the pad. The time measured is recorded as Acquisition Time 1. Thereafter the pad is weighted with a plate for 20 min, the load being further maintained at 13.6 g/cm$^2$. Thereafter the plate is removed, 10 g±0.5 g of filter paper (Schleicher & Schuell, 1450 CV) are placed on the central spot and loaded with a weight (area 10×10 cm, weight 3.5 kg) for 15 s. After this period the weight is removed, and the filter paper is reweighed. The weight difference is noted as Rewet 1. Thereafter the plastic plate with application ring is again placed on the pad and the liquid is applied for the second time. The time measured is noted as Acquisition Time 2. The procedure is repeated as described, but 45 g±0.5 g of filter paper are used for the Rewet test. Rewet 2 is noted. The same method is employed to determine Acquisition Time 3. 50 g±0.5 g of filter paper are used to determine Rewet 3.

INVENTIVE EXAMPLES

Inventive Example 1

A 10 1 capacity polyethylene vessel, well insulated by foamed polymer material, is charged with 3600 g of demineralized water and 1400 g of acrylic acid. 14 g of tetraallyloxyethane are then added as copolymerization crosslinker. At a temperature of 4° C., the initiators, consisting of 2.2 g of 2,2'-azabisamidinopropane dihydrochloride, dissolved in 20 g of demineralized water, 4 g of potassium peroxodisulfate, dissolved in 150 g of demineralized water, and 0.4 g of ascorbic acid, dissolved in 20 g of demineralized water, are added in succession and stirred in. The reaction solution is then left to stand without stirring, and the temperature of the polymerization rises to about 92° C. A solid gel is obtained, and this gel is subsequently mechanically comminuted, adjusted to pH 6.0 by addition of 50% strength by weight sodium hydroxide solution and admixed with 150 g of a 15% strength by weight aqueous solution of a polyamidoamine-epichlorohydrin adduct (RETEN 204 LS from Hercules) as reactive crosslinker. The gel is then dried, ground and classified to a particle size distribution of 100–850 μm. 1 kg of this dried hydrogel is then sprayed in a plowshare mixer with a solution consisting of 40 g of demineralized water, 40 g of methanol and 1.5 g of ethylene glycol diglycidyl ether and then heated at 140° C. for 60 minutes. The product described herein has the following properties:

| | | |
|---|---|---|
| Pressure Absorbency Index | = | 90.2 |
| Vertical Absorption under pressure | = | 16.2 g/g |
| PUP 0.7 psi (4826.5 Pa) | = | 22.2 g/g |
| AUL 21 dyn/cm$^2$ (2100 Pa) | = | 22.3 g/g |
| Acquisition/Rewet under pressure: | | |
| Acquisition Time 1 | = | 23 s |
| Acquisition Time 2 | = | 48 s |
| Acquisition Time 3 | = | 62 s |
| Rewet 1 | = | <0.1 g |
| Rewet 2 | = | 0.3 g |
| Rewet 3 | = | 1.5 g |

Inventive Example 2

A 10 1 capacity polyethylene vessel, well insulated by foamed polymer material, is charged with 3400 g of demineralized water and 1350 g of acrylic acid. This is followed by the addition of 11.5 g of allyl methacrylate as copolymerization crosslinker and 270 g of an alkaline sodium aluminate solution as reactive crosslinker which arithmetically contains 18.7% by weight of Al$_2$O$_3$ and 20% by weight of Na$_2$O. At a temperature of 4° C., the initiators, consisting of 2.2 g of 2,2'-azobisamidinopropane dihydrochloride, dissolved in 20 g of demineralized water, 4 g of potassium peroxodisulfate, dissolved in 150 g of demineralized water, and 0.4 g of ascorbic acid, dissolved in 20 g of demineralized water, are added in succession and stirred in. The reaction solution is then left to stand without stirring. The polymerization takes place adiabatically, the temperature rising to about 90° C. and a solid gel being formed. This gel is subsequently mechanically comminuted and adjusted to pS 6.0 by addition of 50% strength by weight sodium hydroxide solution. The gel is then dried, ground and classified to a particle size distribution of 100–850 μm. 1 kg of this dried hydrogel is sprayed in a plowshare mixer with a solution consisting of 40 g of demineralized water, 60 g of i-propanol and 30 g of a 15% strength by weight aqueous solution of a polyamidoamine-epichlorohydrin adduct (RETEN 204 LS from Hercules) and then heated at 160° C. for 45 minutes. The product described herein has the following properties:

| | | |
|---|---|---|
| Pressure Absorbency Index | = | 93.1 |
| Vertical Absorption under pressure | = | 14.0 g/g |
| PUP 0.7 psi (4826.5 Pa) | = | 21.7 g/g |
| AUL 21,000 dyn/cm$^2$ (2100 Pa) | = | 25.4 g/g |
| Acquisition/Rewet under pressure: | | |
| Acquisition Time 1 | = | 24 s |
| Acquisition Time 2 | = | 51 s |
| Acquisition Time 3 | = | 70 s |
| Rewet 1 | = | <0.1 g |
| Rewet 2 | = | 0.4 g |
| Rewet 3 | = | 1.8 g |

Inventive Example 3

A 10 1 capacity polyethylene vessel, well insulated by foamed polymer material, is charged with 3500 g of demineralized water and 1500 g of acrylic acid. This is followed by the addition of 7.5 g of methylenebisacrylamide as copolymerization crosslinker and of 7 g of 2-hydroxyethyl methacrylate as mixed copolymerization/reactive crosslinker. At a temperature of 20° C., the initiators, consisting of 2.0 g of 2,2'-azobisamidinopropane dihydrochloride, dissolved in 20 g of demineralized water, 4.4 g of potassium peroxodisulfate, dissolved in 150 g of demineralized water, and 0.8 g of ascorbic acid, dissolved in 20 g of demineralized water, are added in succession and stirred in. The reaction solution is then left to stand without stirring. The polymerization takes place adiabatically, the temperature rising to about 98° C. and a solid gel being formed. This gel is subsequently mechanically comminuted and adjusted to pH 6.0 by addition of 50% strength by weight sodium hydroxide solution. The gel is then dried, ground and classified to a particle size distribution of 100–850 μm. 600 g of this dried hydrogel are sprayed in a Patterson & Kelly mixer with a solution consisting of 1 g of bisoxazoline, 1.2 g of aluminum sulfate, 22.5 g of i-propanol and 22.5 g of demineralized water and then heated at 185° C. for 45 minutes. The product described herein has the following properties:

| | | |
|---|---|---|
| Pressure Absorbency Index | = | 85.8 |
| Vertical Absorption under pressure | = | 17.2 g/g |
| PUP 0.7 psi (4826.5 Pa) | = | 21.3 g/g |
| AUL 2100 dyn/cm$^2$ (2100 Pa) | = | 23.6 g/g |
| Acquisition/Rewet under pressure: | | |
| Acquisition Time 1 | = | 22 s |
| Acquisition Time 2 | = | 45 s |
| Acquisition Time 3 | = | 58 s |
| Rewet 1 | = | <0.1 g |
| Rewet 2 | = | 0.4 g |
| Rewet 3 | = | 1.6 g |

Inventive Example 4

A 30 l capacity polyethylene vessel, well insulated by foamed polymer material, is charged with 14,340 g of demineralized water and 72 g of pentaerythritol triallyl ether as copolymerization crosslinker. 5172 g of sodium bicarbonate are suspended in the initial charge, and 5990 g of acrylic acid are gradually metered in at such a rate that overfoaming of the reaction solution is avoided, the reaction solution cooling down to a temperature of about 3–5° C. At a temperature of 4° C., the initiators, 6.0 g of 2,2'-azobisamidinopropane dihydrochloride, dissolved in 60 g of demineralized water, 12 g of potassium peroxodisulfate, dissolved in 450 g of demineralized water, and 1.2 g of ascorbic acid, dissolved in 50 g of demineralized water, are added in succession and thoroughly stirred in. The reaction solution is then left to stand without stirring. The polymerization takes place adiabatically, the temperature rising to about 85° C. and a gel being formed. This gel is subsequently transferred into a kneader, admixed with 60 g of ethylene glycol diglycidyl ether (dissolved in 500 g of demineralized water) as reactive crosslinker, homogeneously kneaded, comminuted, dried in an airstream at 170° C., ground and screened. 1 kg of this product was sprayed in a plowshare mixer with a solution of 2 g of polyglyceryl polyglycidyl ether (Denacol EX-512 from Nagase Chemicals Ltd.), 0.3 g of citric acid, 60 g of demineralized water and 40 g of 1,2-propanediol and then heated at 150° C. for 40 minutes. The product was subsequently blended with 0.1% by weight of hydrophilic silica (Aerosil 200) and the particle size fraction of 120–850 μm was screened out. The product obtained is characterized by the following physical data:

| | | |
|---|---|---|
| Pressure Absorbency Index | = | 96.2 |
| Vertical Absorption under pressure | = | 15.0 g/g |
| PUP 0.7 psi (4826.5 Pa) | = | 20.8 g/g |
| AUL 2100 dyn/cm$^2$ (2100 Pa) | = | 23.5 g/g |
| Acquisition/Rewet under pressure: | | |
| Acquisition Time 1 | = | 27 s |

| -continued | | |
|---|---|---|
| Acquisition Time 2 | = | 51 s |
| Acquisition Time 3 | = | 73 s |
| Rewet 1 | = | <0.1 g |
| Rewet 2 | = | 0.5 g |
| Rewet 3 | = | 1.9 g |

The hydrogels obtained by Inventive Examples 1 to 4 are notable for excellent absorption capacity coupled with excellent liquid transport and conveyance and are therefore highly useful as absorbents for water and aqueous fluids, especially body fluids, for example urine or blood, for example in hygiene articles such as, for example, baby and adult diapers, sanitary napkins, tampons and the like.

Comparative Examples

Comparative Example 1

Inventive Example 1 is repeated except that no polyamidoamine-epichlorohydrin adduct is added to the gel as reactive crosslinker. The product described herein has the following properties:

| | | |
|---|---|---|
| Pressure Absorbenay Index | = | 122.5 |
| Vertical Absorption under pressure | = | 9.0 g/g |
| PUP 0.7 psi (4826.5 Pa) | = | 30.5 g/g |
| AUL 21,000 dyn/cm$^2$ (2100 Pa) | = | 32.5 g/g |
| Acquisition/Rewet under pressure: | | |
| Acquisition Time 1 | = | 29 s |
| Acquisition Time 2 | = | 88 s |
| Acquisition Time 3 | = | 142 s |
| Rewet 1 | = | <0.1 g |
| Rewet 2 | = | 0.6 g |
| Rewet 3 | = | 2.9 g |

Comparative Example 2

Inventive Example 2 is repeated except that no sodium aluminate is added to the monomer solution as reactive crosslinker, The product described herein has the following properties:

| | | |
|---|---|---|
| Pressure Absorbency Index | = | 118.6 |
| Vertical Absorption under pressure | = | 8.0 g/g |
| PUP 0.7 psi (4826.5 Pa) | = | 31.8 g/g |
| AUL 21,000 dyn/cm$^2$ (2100 Pa) | = | 33.7 g/g |
| Acquisition/Rewet under pressure: | | |
| Acquisition Time 1 | = | 32 s |
| Acquisition Time 2 | = | 95 s |
| Acquisition Time 3 | = | 166 s |
| Rewet 1 | = | <0.1 g |
| Rewet 2 | = | 0.7 g |
| Rewet 3 | = | 3.3 g |

Comparative Example 3

Inventive Example 3 is repeated except that no methylenebisacrylamide is added to the monomer solution as copolymerization crosslinker. The product described herein has the following properties:

| | | |
|---|---|---|
| Pressure Absorbency Index | = | 82.5 |
| Vertical Absorption under pressure PUP 0.7 psi (4826.5 Pa) | = | 5.4 g/g 16.4 g/g |
| AUL 2100 dyn/cm² (2100 Pa) | = | 26.8 g/g |
| Acquisition/Rewet under pressure: | | |
| Acquisition Time 1 | = | 37 s |
| Acquisition Time 2 | = | 135 s |
| Acquisition Time 3 | = | 270 s |
| Rewet 1 | = | 0.2 g |
| Rewet 2 | = | 1.2 g |
| Rewet 3 | = | 5.4 g |

Comparative Example 4 inventive Example 4 is repeated except the at no ethylene glycol diglycidyl ether is added to the gel as reactive crosslinker. The product obtained is characterized by the following physical data:

| | | |
|---|---|---|
| Pressure Absorbency Index | = | 127.4 |
| Vertical Absorption under pressure | = | 10.5 g/g |
| PUP 0.7 psi (4826.5 Pa) | = | 35.8 g/g |
| AUL 2100 dyn/cm² (2100 Pa) | = | 34.2 g/g |
| Acquisition/Rewet under pressure: | | |
| Acquisition Time 1 | = | 24 s |
| Acquisition Time 2 | = | 87 s |
| Acquisition Time 3 | = | 115 s |
| Rewet 1 | = | <0.1 g |
| Rewet 2 | = | 0.5 g |
| Rewet 3 | = | 2.8 g |

The hydrogels obtained by Comparative Examples 1 to 4 have considerable disadvantages with regard to liquid transportation and conveyance compared with the hydrogels obtained by inventive Examples 1 to 4, a s evidenced by higher values for Acquisition Time 3 and Rewet 3 in the Acquisition/Rewet test under pressure.

We claim:

1. A crosslinked, hydrophilic, swellable hydrogel comprising polymerized monomers or a graft polymer, wherein said hydrogel has a Pressure Absorbency Index <100 and a Vertical Absorption of not less than 12 g/g under a pressure of 1922.8 Pa.

2. A crosslinked, hydrophilic, swellable hydrogel as claimed in claim 1, characterized by having a Performance Under Pressure value of <23 g/g under a confining pressure of 4826.5 Pa.

3. A crosslinked hydrophilic, swellable hydrogel as claimed in claim 1, having an Absorbency Under Load value of <27 g/g under a confining pressure of 2100 Pa.

4. A crosslinked, hydrophilic, swellable hydrogel as claimed in claim 1, wherein the hydrophile monomer comprises compounds comprising polymerized monomers of general formula

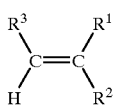

(I)

where $R^1$ is hydrogen, methyl or ethyl, $R^2$ is a —COOR$^4$ group, a phosphonyl group, a phosphonyl group esterified with (C$_1$–C$_4$) alkanol or a group of the formula where $R^3$ is hydrogen, methyl, ethyl or carboxyl, $R^4$ is hydrogen, an alkali metal ion or an ammonium ion, and $R^5$ is sulfonyl, phosphonyl or carboxyl.

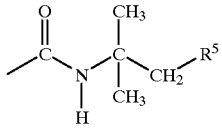

(II)

5. A crosslinked, hydrophilic, swellable hydrogel as claimed in claim 1, wherein the graft polymer is at least one compound selected from the group consisting of starch, starch derivatives, cellulose, cellulose derivatives, polyvinyl alcohol, polyalkylene oxide, polyethylene oxide, polypropylene oxide and hydrophilic polyesters.

6. The crosslinked, hydrophilic, swellable hydrogel of claim 1, made by a process which comprises free-radically polymerizing hydrophilic monomers which contain acid groups, or their alkali metal or ammonium salts, with
(a) a copolymerization crosslinker which contains at least two ethylenically unsaturated double bonds in the molecule, and
(b) a reactive crosslinker A which contains an ethylenically unsaturated double bond and at least one functional group capable of forming covalent bonds with a hydrophilic polymer, a reactive crosslinker B which contains at least two functional groups capable of forming covalent bonds with acid groups of a hydrophilic polymer, and/or with ions of polyvalent metals
optionally in the presence of at least one grafting base to form a crosslinked, hydrophilic base polymer, comminuting said base polymer and postcrosslinking the surface of the particles of said base polymer.

7. The crosslinked, hydrophilic, swellable hydrogel of claim 1, which comprises free-radically polymerizing hydrophilic monomers which contain acid groups, or their alkali metal or ammonium salts, with
(a) a copolymerization crosslinker which contains at least two ethylenically unsaturated double bonds in the molecule, and optionally
(b) a reactive crosslinker A which contains an ethylenically unsaturated double bond and at least one functional group capable of forming covalent bonds with acid groups of a hydrophilic polymer,
optionally in the presence of a grafting base to form a crosslinked, hydrophilic base polymer, comminuting said base polymer, during said comminuting or thereafter mixing it with a reactive crosslinker B and/or with ions of polyvalent metals and postcrosslinking the surface of the particles of said base polymer.

8. A hydrogel as claimed in claim 6, wherein the copolymerization crosslinker is a compound having at least two allyl, methacrylate and/or acrylate groups.

9. A hydrogel as claimed in claim 6, wherein said reactive crosslinker B is a polyamidoamine or its reaction product with epichlorohydrin or bischlorohydrin ethers of alkylene glycols or polyalkylene glycols.

10. A hydrogel as claimed in claim 6, wherein crosslinker (b) is sodium aluminate.

11. A hydrogel as claimed in claim 6, wherein the polymerization of the hydrophilic monomers which contain acid groups is carried out in the presence of
(a) allyl methacrylate, tetraallyloxyethane, methylenebisacrylamide, pentaerythritol triallyl ether or mixtures thereof, and
(b) hydroxyethyl acrylate, hydroxyethyl methacrylate, hydroxypropyl acrylate, hydroxypropyl methacrylate, hydroxybutyl acrylates or mixtures thereof as crosslinker.

12. A hydrogel as claimed in claim 7, wherein said postcrosslinking of said surface of said particles of said base polymer is affected with sodium aluminate.

13. A hydrogel as claimed in claim 6, wherein said postcrosslinking of said surface of the particulate hydrophilic base polymer is effected with diglycidyl ethers, reaction products of polyamidoamines with epichlorohydrin, bischlorohydrin ethers of alkylene glycols or polyalkylene glycols, polyethyleneimines, polymers containing vinylamine units or mixtures thereof.

14. A hydrogel as claimed in claim 6, wherein said crosslinked, hydrophilic base polymer is produced in the presence of
(a) at least one copolymerization crosslinker and
(b) at least one reactive crosslinker B.

* * * * *